United States Patent
Fujioka

(10) Patent No.: US 11,690,838 B2
(45) Date of Patent: Jul. 4, 2023

(54) THERAPEUTIC AGENT FOR FIBROSIS

(71) Applicant: TAIHO PHARMACEUTICAL CO., LTD., Tokyo (JP)

(72) Inventor: Akio Fujioka, Tsukuba (JP)

(73) Assignee: TAIHO PHARMACEUTICAL CO., LTD., Tokyo (JP)

(*) Notice: Subject to any disclaimer, the term of this patent is extended or adjusted under 35 U.S.C. 154(b) by 55 days.

(21) Appl. No.: 17/513,946

(22) Filed: Oct. 29, 2021

(65) Prior Publication Data
US 2022/0047572 A1 Feb. 17, 2022

Related U.S. Application Data

(63) Continuation of application No. 16/889,870, filed on Jun. 2, 2020, now Pat. No. 11,191,759, which is a continuation of application No. 16/573,362, filed on Sep. 17, 2019, now Pat. No. 10,695,340, which is a continuation of application No. 15/574,060, filed as application No. PCT/JP2016/068902 on Jun. 24, 2016, now Pat. No. 10,449,189.

(30) Foreign Application Priority Data

Jun. 25, 2015 (JP) .................................. 2015-127788

(51) Int. Cl.
- *A61K 31/47* (2006.01)
- *A61P 11/00* (2006.01)
- *C07D 215/50* (2006.01)

(52) U.S. Cl.
CPC .............. *A61K 31/47* (2013.01); *A61P 11/00* (2018.01); *C07D 215/50* (2013.01)

(58) Field of Classification Search
CPC ........ A61K 31/47; C07D 215/50; A61P 13/12
See application file for complete search history.

(56) References Cited

U.S. PATENT DOCUMENTS

| | | |
|---|---|---|
| 8,304,427 B2 | 11/2012 | Suda |
| 2005/0113284 A1 | 5/2005 | Nakamura et al. |
| 2007/0191369 A1 | 8/2007 | Lauffer et al. |
| 2009/0118305 A1 | 5/2009 | Barlaam et al. |
| 2010/0063054 A1 | 3/2010 | Bressi |
| 2010/0190774 A1 | 7/2010 | Lauffer et al. |
| 2011/0034439 A1 | 2/2011 | Suda et al. |
| 2011/0212967 A1 | 9/2011 | Zhuo et al. |

(Continued)

FOREIGN PATENT DOCUMENTS

| | | |
|---|---|---|
| EP | 1 466 624 A1 | 10/2004 |
| JP | 2003-238592 A | 8/2003 |

(Continued)

OTHER PUBLICATIONS

International Search Report dated Sep. 13, 2016 in PCT/JP2016/068902 filed Jun. 24, 2016.

(Continued)

*Primary Examiner* — San Ming R Hui
(74) *Attorney, Agent, or Firm* — Oblon, McClelland, Maier & Neustadt, L.L.P.

(57) ABSTRACT

Provided are a therapeutic agent and a pharmaceutical composition exerting an excellent prophylactic or therapeutic effect on fibrosis and symptoms associated with fibrosis. The therapeutic agent for fibrosis comprises 4-[2-fluoro-4-[[[(2-phenylacetyl)amino]thioxomethyl]amino]-phenoxy]-7-methoxy-N-methyl-6-quinolinecarboxamide or a salt thereof as an active ingredient.

8 Claims, 2 Drawing Sheets

**; $p < 0.01$ in the disease control group by Student's $t$-test as compared with the normal group
; $p < 0.01$ in the disease control group by Student's $t$-test as compared with the sham group
†; $p < 0.05$ in the treatment group by Dunnett's test as compared with the disease control group

(56) References Cited

U.S. PATENT DOCUMENTS

| | | |
|---|---|---|
| 2011/0281865 A1 | 11/2011 | Muthuppalaniappan et al. |
| 2013/0261116 A1 | 10/2013 | Muthuppalaniappan et al. |
| 2013/0345224 A1 | 12/2013 | Zhuo et al. |
| 2014/0378409 A1 | 12/2014 | Fujita et al. |
| 2015/0133449 A1 | 5/2015 | Muthuppalaniappan et al. |
| 2015/0164879 A1 | 6/2015 | Miyaura et al. |
| 2016/0137650 A1 | 5/2016 | Zhuo et al. |

FOREIGN PATENT DOCUMENTS

| | | |
|---|---|---|
| JP | 2009-500347 A | 1/2009 |
| JP | 2009-518296 A | 5/2009 |
| JP | 2010-519204 A | 6/2010 |
| JP | 2011-500778 A | 1/2011 |
| JP | 2013-518887 A | 5/2013 |
| JP | 2013-529207 A | 7/2013 |
| RU | 2 494 470 C1 | 9/2013 |
| WO | WO 99/55361 A1 | 11/1999 |
| WO | WO 2007/064797 A2 | 6/2007 |
| WO | WO 2009/053737 A2 | 4/2009 |
| WO | WO 2009/125597 A1 | 10/2009 |
| WO | WO 2011/145035 A1 | 11/2011 |
| WO | WO 2011/162835 A1 | 12/2011 |
| WO | WO 2013/100014 A1 | 7/2013 |
| WO | WO 2015/046484 A1 | 4/2015 |

OTHER PUBLICATIONS

P. Spagnolo, et al., "idiopathic pulmonary fibrosis: Recent advances on pharmacological therapy" Pharmacology & Therapeutics, 2015, 10 Pages.

Richard Hubbard, et al., "Lung Cancer and Cryptogenic Fibrosing Alveolitis, A Population-based Cohort Study" American Journal of Respiratory and Critical Care Medicine, vol. 161, 2000, pp. 5-8.

David M. Spain, "The association of terminal bronchiolar carcinoma with chronic interstitial inflammation and fibrosis of the lungs" Am Rev Tuberc, 1957, pp. 559-567.

Arnab Datta, et al., "Novel therapeutic approaches for pulmonary fibrosis" British Journal of Pharmacology. vol. 163, 2011, pp. 141-172.

Extended European Search Report dated Jan. 30, 2019 in Patent Application No. 16814513.4, 8 pages.

Zhao, L. et al. "Paracrine activation of MET promotes peritoneal carcinomatosis in scirrhous gastic cancer" Cancer Science, vol. 104, No. 12, XP002787868, 2013, pp. 1640-1646.

Combine Russian Federation Office Action and Search Report dated Nov. 29, 2019 in Patent Application No. 2017145271/04(077515) (with English translation), 12 pages.

Notice of Reasons for Refusal dated Jan. 26, 2021 in Japanese Patent Application No. 2017-525457 (with English language translation), 6 pages.

Hidenori Fujita, et al., "the Novel VEGF Receptor/MET-Targeted Kinase Inhibitor TAS-115 Has Marked In Vivo Antitumor Properties and a Favorable Tolerability Profile," Molecular Cancer Therapeutics, vol. 12, No. 12, Dec. 2013, 13 pages.

Japanese Office Action dated Nov. 1, 2022 in Japanese Patent Application No. 2021-180108 (with uneditedcomputer generated English translation), 8 pages.

Masataka Kuwana, "Scleroderma (Systemic sclerosis)", Medical Practice, 2006, vol. 23(4), pp. 669-673 (with uneditedcomputer generated English abstract).

Extended European Search Report dated Feb. 24, 2022 in European Patent Application No. 21205221.1, 7 pages.

Masatoshi Jinnin, et al., "Effects of Hepatocyte Growth Factor on the Expression of Type I Collagen and Matrix Metalloproteinase-1 in Normal and Scleroderma Dermal Fibroblasts" Journal of Investigative Dermatology, vol. 124, No. 2, Feb. 1, 2005, pp. 324-330.

[Figure 1]
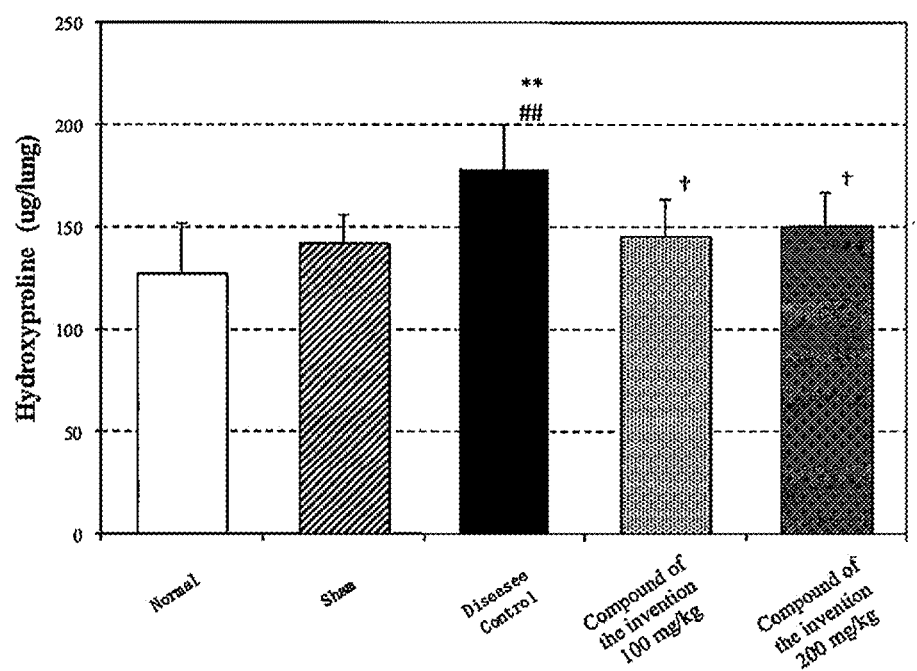
**; $p < 0.01$ in the disease control group by Student's $t$-test as compared with the normal group
; $p < 0.01$ in the disease control group by Student's $t$-test as compared with the sham group
†; $p < 0.05$ in the treatment group by Dunnett's test as compared with the disease control group

[Figure 2]
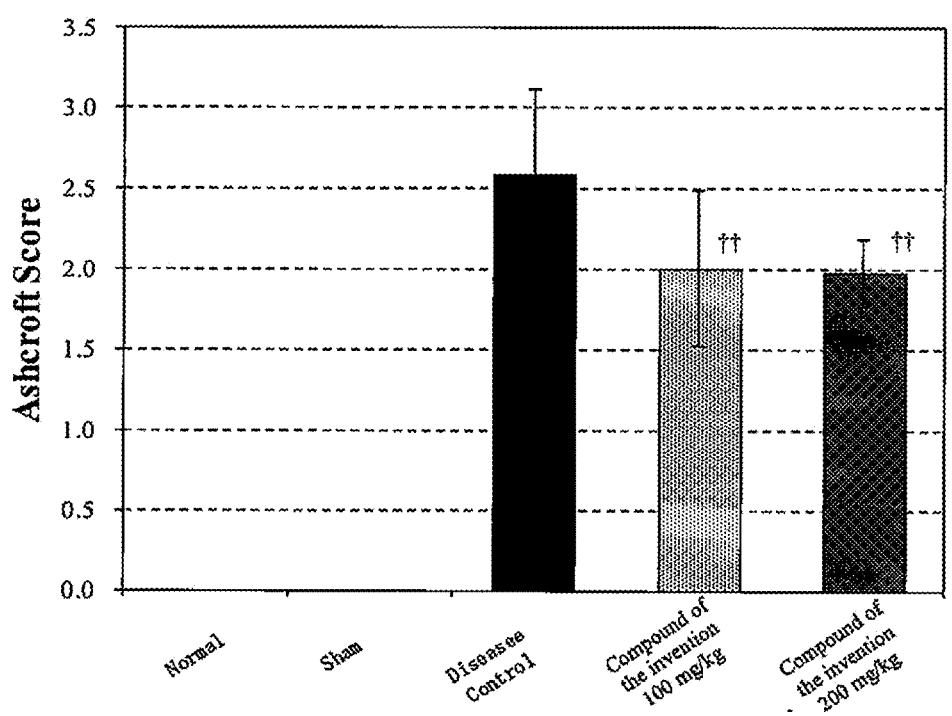
†† ; p < 0.01 in the treatment group by Dunnett's test as compared with the disease control group

THERAPEUTIC AGENT FOR FIBROSIS

CROSS REFERENCES TO RELATED APPLICATIONS

This application is a continuation of U.S. patent application Ser. No. 16/889,870, filed on Jun. 2, 2020 (now issued as U.S. Pat. No. 11,191,759), which is a continuation of U.S. patent application Ser. No. 16/573,362, filed on Sep. 17, 2019 (now issued as U.S. Pat. No. 10,695,340), which is a continuation of U.S. patent application Ser. No. 15/574,060, filed on Nov. 14, 2017 (now issued as U.S. Pat. No. 10,449,189), which is the National Stage of International Patent Application No. PCT/JP2016/068902, filed on Jun. 24, 2016, and claims priority to Japanese Patent Application No. 2015-127788, filed on Jun. 25, 2015, all of which are incorporated herein by reference in their entireties.

FIELD OF THE INVENTION

The present invention relates to a therapeutic agent for fibrosis and a pharmaceutical composition for treating fibrosis.

BACKGROUND OF THE INVENTION

Fibrosis is defined as abnormal accumulation of a fibrous tissue caused by e.g., tissue damage and autoimmune reaction. In humans, abnormal accumulation of a fibrous tissue is found in various organs and tissues such as lung, liver, pancreas, kidney, bone marrow and skin.

Lung fibrosis is a disease characterized by diffuse fibroplasia in the alveolar wall and major symptoms such as dry cough and dyspnea on exertion. Lung fibrosis, in a narrow sense, refers to idiopathic lung fibrosis, which is a terminal disease state of interstitial pneumonia and, in a broad sense, refers to a comorbid state of abnormal accumulation of a fibrous tissue in lung and interstitial pneumonia. All interstitial pneumonitis may be causes of inducing lung fibrosis.

Interstitial pneumonia is a collective term for diseases causing inflammation around the pulmonary interstitium and includes interstitial pneumonia due to specific causes such as infection, collagenosis, radiation, a medicinal agent and dust, and idiopathic interstitial pneumonia due to unknown causes. As the idiopathic interstitial pneumonia, idiopathic lung fibrosis, nonspecific interstitial pneumonia, cryptogenic organized pneumonia, interstitial lung disease accompanied by respiratory bronchiolitis, desquamative interstitial pneumonia, acute interstitial pneumonia and lymphoid interstitial pneumonia, are known. Of these, idiopathic lung fibrosis most frequently occurs and is sometimes simply referred to as lung fibrosis.

In idiopathic lung fibrosis, a fibrous connective tissue is diffusely and excessively formed in the pulmonary interstitium, impairing lung function. An average survival period after diagnosis of idiopathic lung fibrosis is reported to be 2.5 to 5 years (Non Patent Document 1). In particular, the average survival period after acute exacerbation is extremely short and falls within two months. In lung fibrosis in association with an interstitial pneumonia and emphysema, it is reported that lung cancer is developed as a complication at a high rate (Non Patent Documents 2, 3).

Interstitial pneumonia induced by a specific cause, can be mostly cured by removing the cause and administering, for example, an anti-inflammatory agent such as a steroid drug. In contrast, lung fibrosis and interstitial pneumonia accompanied by abnormal accumulation of a fibrous tissue is usually treated with a steroid drug and an immunosuppressant. However effective treatments for improving prognosis have not yet been obtained at present and development of a novel therapeutic agent is desired.

4-[2-Fluoro-4-[[[(2-phenylacetyl)amino]thioxomethyl]amino]-phenoxy]-7-methoxy-N-methyl-6-quinolinecarboxamide is an antitumor agent with reduced side effects (Patent Document 1) and also known to exhibit an excellent enhancing activity of an antitumor effect if used in combination with another antitumor agent (Patent Document 2). In addition, it is recently found that the compound is also useful as a therapeutic agent for osteoporosis (Patent Document 3).

However, it is totally unknown that the compound is effective for lung fibrosis and interstitial pneumonia. In the meantime, it is suggested that the symptom of lung fibrosis is improved by administration of HGF (Non Patent Document 2), and that activation of HGF/c-Met is effective for treating lung fibrosis (Non Patent Document 4).

CITATION LIST

Patent Document

[Patent Document 1] International Publication No. WO2009/125597
[Patent Document 2] International Publication No. WO2013/100014
[Patent Document 3] International Publication No. WO2015/046484

Non Patent Document

[Non Patent Document 1] Pharmacol Ther. 2015 May 3. pii: S0163-7258(15)00091-1
[Non Patent Document 2] Am J Respir Crit Care Med. 2000 January; 161(1):5-8
[Non Patent Document 3] Am Rev Tuberc 1957; 76: 559-66
[Non Patent Document 4] British J. Pharmacology 2011; 163: 141-172

SUMMARY OF THE INVENTION

Problems to be Solved by the Invention

An object of the present invention is to provide a therapeutic agent and a pharmaceutical composition exhibiting an excellent prophylactic or therapeutic effect on fibrosis.

Means for Solving the Problem

The present inventors conducted intensive studies with a view to solving the aforementioned problems. As a result, they found that 4-[2-fluoro-4-[[[(2-phenylacetyl)amino]thioxomethyl]amino]-phenoxy]-7-methoxy-N-methyl-6-quinolinecarboxamide or a salt thereof exhibits an effect for suppression of abnormal accumulation of a fibrous tissue and an inflammation suppression effect associated therewith and is useful for preventing or treating fibrosis and the inflammation associated therewith.

More specifically, the present invention relates to the following 1) to 5).
1) A therapeutic agent for fibrosis comprising 4-[2-fluoro-4-[[[(2-phenylacetyl)amino]thioxomethyl]amino]-phenoxy]-7-methoxy-N-methyl-6-quinolinecarboxamide or a salt thereof as an active ingredient.

1)-2
The therapeutic agent for fibrosis according to 1), wherein the fibrosis is lung fibrosis.
1)-3
The therapeutic agent for fibrosis according to 1) or 1)-2, wherein the fibrosis is interstitial pneumonia accompanied by abnormal accumulation of a fibrous tissue.
1)-4
The therapeutic agent for fibrosis according to 1) to 1)-3, wherein the fibrosis is idiopathic lung fibrosis.
2) A pharmaceutical composition for treating fibrosis, comprising 4-[2-fluoro-4-[[[(2-phenylacetyl)amino]thioxomethyl]amino]-phenoxy]-7-methoxy-N-methyl-6-quinolinecarboxamide or a salt thereof and a pharmaceutically acceptable carrier.
2)-2
The pharmaceutical composition according to 2), wherein the fibrosis is lung fibrosis.
2)-3
The pharmaceutical composition according to 2) or 2)-2, wherein the fibrosis is interstitial pneumonia accompanied by abnormal accumulation of a fibrous tissue.
2)-4
The pharmaceutical composition according to 2) to 2)-3, wherein the fibrosis is idiopathic lung fibrosis.
3) 4-[2-Fluoro-4-[[[(2-phenylacetyl)amino]thioxomethyl]amino]-phenoxy]-7-methoxy-N-methyl-6-quinolinecarboxamide or a salt thereof for use in treatment of fibrosis.
3)-2
4-[2-Fluoro-4-[[[(2-phenylacetyl)amino]thioxomethyl]amino]-phenoxy]-7-methoxy-N-methyl-6-quinolinecarboxamide or a salt thereof according to 3), wherein the fibrosis is lung fibrosis.
3)-3
4-[2-Fluoro-4-[[[(2-phenylacetyl)amino]thioxomethyl]amino]-phenoxy]-7-methoxy-N-methyl-6-quinolinecarboxamide or a salt thereof according to 3) or 3)-2, wherein the fibrosis is interstitial pneumonia accompanied by abnormal accumulation of a fibrous tissue.
3)-4
4-[2-Fluoro-4-[[[(2-phenylacetyl)amino]thioxomethyl]amino]-phenoxy]-7-methoxy-N-methyl-6-quinolinecarboxamide or a salt thereof according to 3) to 3)-3, wherein the fibrosis is idiopathic lung fibrosis.
4) A pharmaceutical composition for use in treatment of fibrosis, comprising 4-[2-fluoro-4-[[[(2-phenylacetyl)amino]thioxomethyl]amino]-phenoxy]-7-methoxy-N-methyl-6-quinolinecarboxamide or a salt thereof and a pharmaceutically acceptable carrier.
4)-2
The pharmaceutical composition according to 4), wherein the fibrosis is lung fibrosis.
4)-3
The pharmaceutical composition according to 4) or 4)-2, wherein the fibrosis is interstitial pneumonia accompanied by abnormal accumulation of a fibrous tissue.
4)-4
The pharmaceutical composition according to 4) to 4)-3, wherein the fibrosis is idiopathic lung fibrosis.
5) A method for treating fibrosis, comprising administering 4-[2-fluoro-4-[[[(2-phenylacetyl)amino]thioxomethyl]amino]-phenoxy]-7-methoxy-N-methyl-6-quinolinecarboxamide or a salt thereof to a patient.
5)-2
The method for treating fibrosis according to 5), wherein the fibrosis is lung fibrosis.
5)-3
The method for treating fibrosis according to 5) or 5)-2, wherein the fibrosis is interstitial pneumonia accompanied by abnormal accumulation of a fibrous tissue.
5)-4
The method for treating fibrosis according to 5) to 5)-3, wherein the fibrosis is idiopathic lung fibrosis.

Effects of the Invention

The compound of the present invention exerts an excellent suppressing effect on progression of abnormal accumulation of fibrous tissues in tissues. Thus, according to the present invention, abnormal accumulation of fibrous tissues can be effectively treated and, in particular, idiopathic lung fibrosis and interstitial pneumonia accompanied by abnormal accumulation of a fibrous tissue can be effectively treated.

BRIEF DESCRIPTION OF DRAWINGS

FIG. 1 The figure is a graph showing the amount of hydroxyproline in lung tissues.
FIG. 2 The figure is a graph showing scores of abnormal accumulation of a fibrous tissue in lung tissues.

DETAILED DESCRIPTION OF THE INVENTION

4-[2-Fluoro-4-[[[(2-phenylacetyl)amino]thioxomethyl]amino]-phenoxy]-7-methoxy-N-methyl-6-quinolinecarboxamide of the present invention (referred to as "the compound of the present invention") or a salt thereof is represented by the following formula (1):

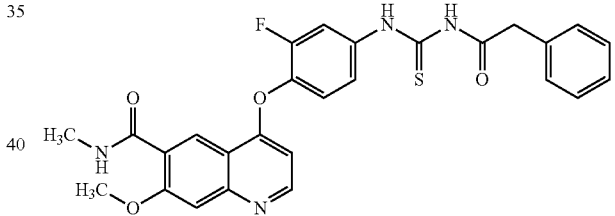

The compound of the present invention is known in the art and can be produced in accordance with a method described, for example, in International Publication No. WO2009/125597 (Patent Document 1).

Examples of the "salt" of the compound of the present invention include an inorganic acid salt, an organic acid salt or an acidic amino acid salt. Examples of the inorganic acid include hydrochloric acid, sulfuric acid, hydrobromic acid, hydroiodic acid, nitric acid and phosphoric acid. Examples of the organic acid include formic acid, acetic acid, propionic acid, malonic acid, succinic acid, glutaric acid, fumaric acid, maleic acid, lactic acid, malic acid, citric acid, tartaric acid, benzenesulfonic acid, p-toluenesulfonic acid and methanesulfonic acid. Examples of the acidic amino acid include glutamic acid and aspartic acid. Among them, an organic acid salt is preferable, a methanesulfonate salt is more preferable and a monomethanesulfonate salt is particularly preferable.

The compound of the present invention also includes hydrates, solvates and crystal polymorphism.

As will be shown later in Examples, the compound of the present invention exerts a suppressive effect on abnormal accumulation of a fibrous tissue and inflammation suppressive effect in tissues.

Accordingly, the compound of the present invention or a salt thereof is useful as a medicine exhibiting excellent prophylactic or therapeutic effects on diseases related to abnormal accumulation of a fibrous tissue and inflammation in tissues, more specifically, as a therapeutic agent for fibrosis and symptoms associated with fibrosis; and particularly can be used for preventing or treating diseases associated with abnormal accumulation of a fibrous tissue in lung tissues, more specifically, lung fibrosis and interstitial pneumonia accompanied by abnormal accumulation of a fibrous tissue.

In the present invention, examples of fibrosis include lung fibrosis, hepatic fibrosis, abnormal accumulation of a fibrous tissue in pancreas, renal fibrosis, prostatic hyperplasia caused by abnormal accumulation of a fibrous tissue, bone marrow fibrosis and scleroderma. In these fibroses, symptoms associated with fibrosis, such as inflammation and atrophy, are observed depending upon the organ with advanced abnormal accumulation of a fibrous tissue and the rate of progression. Thus, treatment for symptom associated with fibrosis is also included in the present invention.

In the present invention, lung fibrosis includes not only idiopathic lung fibrosis but also fibrotic symptom of the lung including comorbidity with interstitial pneumonia. More specifically, the lung fibrosis of the present invention includes interstitial pneumonia possibly causing abnormal accumulation of a fibrous tissue in lung in conjunction therewith.

Examples of such interstitial pneumonia include infectious interstitial pneumonia; interstitial pneumonia associated with collagenosis; interstitial pneumonia associated with radiation exposure; drug-induced interstitial pneumonia; idiopathic interstitial pneumonia such as idiopathic lung fibrosis, nonspecific interstitial pneumonia, idiopathic organized pneumonia, interstitial lung disease accompanied by respiratory bronchiolitis, desquamative interstitial pneumonia, acute interstitial pneumonia and lymphoid interstitial pneumonia. Among them, idiopathic interstitial pneumonia is preferable.

In the present invention, lung fibrosis is preferably chronic situations of these interstitial pneumonitis (in particular, idiopathic interstitial pneumonia), interstitial pneumonia accompanied by abnormal accumulation of a fibrous tissue (in particular, idiopathic interstitial pneumonia), more preferably interstitial pneumonia accompanied by abnormal accumulation of a fibrous tissue (in particular, idiopathic interstitial pneumonia) and particularly preferably idiopathic lung fibrosis.

In the present invention, lung fibrosis is accompanied by symptoms such as collagen production, a reduction in lung weight, pulmonary hypertension and right heart failure. Mitigation of these symptoms is included in the present invention. In interstitial pneumonia accompanied by idiopathic lung fibrosis and abnormal accumulation of a fibrous tissue, the levels of serum markers (e.g., KL-6, SP-A, SP-D) are known to increase. Therefore, in the present invention, therapeutic effects can be indirectly checked based on the aforementioned symptoms or the serum markers.

In the present invention, abnormal accumulation of a fibrous tissue in liver is caused by hepatocellular damage and hepatitis and includes alcohol-induced hepatic fibrosis, congenital hepatic fibrosis and virus-induced fibrosis. In the present invention, hepatic fibrosis is possibly accompanied by hepatitis, fatty liver, liver cirrhosis and hepatic atrophy. Therapies for these symptoms are also included in the present invention. Therefore, in the present invention, therapeutic effect on the aforementioned symptoms can be indirectly checked by measuring e.g., the number of platelets in blood, hyaluronic acid and collagen.

In the present invention, abnormal accumulation of a fibrous tissue in pancreas is abnormal accumulation of a fibrous tissue in the connective tissue in pancreatic interstitium and include e.g., pancreatic cystic fibrosis. In the present invention, abnormal accumulation of a fibrous tissue in pancreas is possibly accompanied by e.g., pancreatitis, pancreatic atrophy and diabetes. Therapies for these symptoms are also included in the present invention. Therefore, therapeutic effects can be indirectly checked by measuring e.g., trypsin and glucose levels in blood.

In the present invention, examples of renal fibrosis include glomerulosclerosis, interstitial renal fibrosis and tubulointerstitial fibrosis. In the present invention, renal fibrosis is possibly accompanied by e.g., nephritis, renal atrophy and renal failure. Therapies for these symptoms are also included in the present invention. Therefore, in the present invention, therapeutic effects on the aforementioned symptoms can be indirectly checked by measuring e.g., collagen level in blood.

In the present invention, prostatic hypertrophy induced by abnormal accumulation of a fibrous tissue is caused by abnormal accumulation of a fibrous tissue in the interstitium of prostatic hypertrophy. In the present invention, prostatic hypertrophy induced by abnormal accumulation of a fibrous tissue is possibly accompanied by e.g., prostatic fibroma, prostatitis and prostatic calcification. Therapies for these symptoms are also included in the present invention.

In the present invention, examples of bone marrow fibrosis include primary bone marrow fibrosis and idiopathic bone marrow fibrosis. In the present invention, bone marrow fibrosis is possibly accompanied by e.g., splenic tumor, splenic infarction, white erythroblastosis, anemia and portal hypertension. Therapies for these symptoms are also included in the present invention. Therefore, in the present invention, therapeutic effects on the aforementioned symptoms can be indirectly checked by measuring e.g., red blood cells, platelets and serum LDH in blood.

In the present invention, examples of scleroderma include disseminated scleroderma and focal scleroderma. In the present invention, scleroderma is possibly accompanied by inflammation of e.g., blood vessels, organ failure, calcification and abnormal accumulation of a fibrous tissue in skin. Therapies for these symptoms are also included in the present invention. Therefore, in the present invention, therapeutic effects on the aforementioned symptoms can be indirectly checked by measuring an anti-nuclear antibody, an anti-topoisomerase I antibody and an anti-centromere antibody.

In the specification, the "therapy" includes not only prevention and treatment for the aforementioned fibroses but also maintenance for suppression of progression of abnormal accumulation of a fibrous tissue in tissues, mitigation of inflammation, mitigation of symptom associated with fibrosis and relapse prevention.

The compound of the present invention or a salt thereof can be prepared into either an oral or a parenteral dosage form and can be produced into various types of dosing preparations by using a pharmaceutically acceptable carrier in accordance with a method known in the art. Examples of the dosage form may include, but are not particularly limited to, oral agents such as tablets, coated tablets, pills, powders, granules, capsules, liquid preparations, suspensions and emulsions; and parenteral agents such as injections, suppositories and inhalants.

When forming tablets, the following carriers can be used: an excipient such as lactose, white sugar, sodium chloride, glucose, urea, starch, calcium carbonate, kaolin, crystalline cellulose and silicic acid; a binder such as water, ethanol, propanol, corn starch, simple syrup, dextrose solution, a starch solution, a gelatin solution, carboxymethylcellulose, shellac, methylcellulose, hydroxypropylcellulose, hydroxypropylmethylcellulose, potassium phosphate and polyvinylpyrrolidone; a disintegrant such as dry starch, sodium alginate, agar powder, laminaran powder, sodium hydrogen carbonate, calcium carbonate, a polyoxyethylene sorbitan fatty acid ester, sodium lauryl sulfate, glycerol monostearate and lactose; a disintegration inhibitor such as white sugar, stearic acid, cacao butter and hydrogenated oil; an absorption promoter such as quaternary ammonium salt and sodium lauryl sulfate; a humectant such as glycerin and starch; an adsorbent such as starch, lactose, kaolin, bentonite and colloidal silicic acid; and a lubricant such as purified talc, a stearate, boric acid powder and polyethylene glycol.

Furthermore, the tablets may be covered with usual coating, if necessary; for example, sugar-coated tablets, gelatin-coated tablets, enteric coated tablets, film-coated tablets, double-layered tablets and multilayered tablets can be prepared.

When forming pills, as the carrier, an excipient such as glucose, lactose, starch, cocoa butter, hydrogenated vegetable oil, kaolin and talc; a binder such as gum Arabic powder, tragacanth powder, gelatin and ethanol; and a disintegrant such as laminaran and agar, can be used. Capsules are prepared by charging hard gelatin capsules or soft capsules with a mixture with the aforementioned various types of carriers, in accordance with a routine method.

When preparing liquid preparations, e.g., oral liquid, syrup and elixir can be prepared by using e.g., a flavoring agent, a buffer and a stabilizer in accordance with a routine method. In this case, examples of the flavoring agent may include white sugar, orange peel, citric acid and tartaric acid; examples of the buffer may include sodium citrate; and examples of the stabilizer may include tragacanth, gum Arabic and gelatin.

When preparing suppositories, as the carrier, polyethylene glycol, cocoa butter, a higher alcohol, an ester of a higher alcohol, gelatin and a semisynthetic glyceride can be used.

When preparing injections, a liquid preparation, an emulsion and a suspension are sterilized and preferably they are isotonic fluids with blood. In preparing these dosage forms, as the diluent, water, an aqueous lactic acid solution, ethyl alcohol, propylene glycol, macrogol, ethoxylated isostearyl alcohol, polyoxyethylenated isostearyl alcohol and a polyoxyethylene sorbitan fatty acid ester can be used.

Note that, in this case, a sufficient amount of salt, glucose or glycerin to prepare an isotonic solution may be added to a pharmaceutical preparation or e.g., a solubilizer, a buffer and a soothing agent usually used may be added.

In preparing an inhalation, an aerosol, a powder inhalant and a liquid inhalant are mentioned as a dosage form.

If necessary, a coloring agent, a preservative, a fragrance, a flavoring agent and a sweetening agent; and other pharmaceutical products may be added to each of these preparations.

Methods for administering the therapeutic agent for fibrosis and the pharmaceutical composition for treating fibrosis of the present invention are appropriately determined depending upon e.g., the dosage form; the age, sex and other conditions of the patient; and symptom of the patient. For example, tablets, pills, powders, granules, capsules, liquid preparations, suspensions and emulsions are orally administered. Injections are intravenously administered singly or in combination with a general complemental liquid such as glucose and amino acids, and further, if necessary, injections are intra-arterially, intramuscularly, intradermally, subcutaneously or intraperitoneally administered by themselves. Suppositories are intra-rectally administered.

The amount of the compound of the present invention or a salt thereof to be blended in a unit-dose of a dosage form as mentioned above varies depending upon the symptom of the patient to be applied or the dosage form; however, the amount per unit dose is desirably about 0.005 to 1,000 mg in the case of an oral preparation, about 0.001 to 500 mg in the case of an injection and about 0.01 to 1,000 mg in the case of a suppository. The dose per day of a medicinal agent having a dosage form as mentioned above varies depending upon e.g., the symptom, body weight, age and sex of the patient and cannot be unconditionally determined; however, the dose/adult/day may be usually about 0.005 to 5,000 mg and preferably 0.01 to 1,000 mg. This may be preferably administered once a day or daily in about 2 to 4 divided doses.

The present invention will be more specifically described below by way of Examples and Test Examples; however, the present invention is not limited to these embodiments.

EXAMPLES

Production Example 1: Synthesis of 4-[2-fluoro-4-[[[(2-phenylacetyl)amino]thioxomethyl]amino]-phenoxy]-7-methoxy-N-methyl-6-quinolinecarboxamide In accordance with the production method described in Patent Document 1, 4-[2-fluoro-4-[[[(2-phenylacetyl)amino]thioxomethyl]amino]-phenoxy]-7-methoxy-N-methyl-6-quinolinecarboxamide was synthesized.

Test Example 1: Suppression Effect on Bleomycin-Induced Mouse Pathology (Lung Fibrosis) Model Mice (C57BL, 6 weeks old) were anesthetized by intraperitoneally administrating pentobarbital (50 mg/kg/day), and then bleomycin (20 μg/25 μL per mouse) was intratracheally sprayed by a sprayer. A week later, the mice were anesthetized by inhalation of isoflurane, 0.2 mL of blood was taken from the eye orbit of the mice. The blood level of a surfactant protein-D (SP-D) was measured. The mice were divided into groups (9 mice) such that the groups have an equal average SP-D value.

The compound of the present invention was orally administered at each of doses of 100 and 200 mg/kg/day, every day for 35 days. In order to confirm whether a pathological model was established, an untreated group (Normal group) and a Sham group were set up. To the mice of the Sham group, physiological saline was intratracheally sprayed in place of bleomycin. The next day after completion of the final administration, the mice were anesthetized by inhalation of isoflurane and euthanized. Thereafter, the lungs were excised out and subjected to pathological analysis for tissues. Abnormal accumulation of a fibrous tissue was evaluated and the amounts of hydroxyproline in the tissues were measured. The abnormal accumulation of a fibrous tissue was evaluated by using Ashcroft's method (J Clin Pathol 1988; 41: 467-470).

The hydroxyproline amounts of lung tissues of individual groups are shown in FIG. 1 and scores of abnormal accumulation of a fibrous tissue in the lung tissues are shown in FIG. 2. The mice to which bleomycin was sprayed, the hydroxyproline level of the lung tissues significantly increased and scores of abnormal accumulation of a fibrous tissue also increased, compared to the sham group. From this, it was determined that abnormal accumulation of a fibrous tissue in the lung tissue in mice was induced by bleomycin treatment and pathological models are established.

The hydroxyproline amounts of groups to which the compound of the present invention was administered at doses of 100 and 200 mg/kg/day, both were significantly low compared to the control group (pathological condition) and their scores of abnormal accumulation of a fibrous tissue were significantly low. From this, it was suggested that the compound of the present invention suppresses abnormal accumulation of a fibrous tissue.

According to the above, the compound of the present invention was demonstrated to be useful as a therapeutic agent for fibrosis, and particularly useful as a therapeutic agent for lung fibrosis.

The invention claimed is:

1. A method for treating abnormal accumulation of a fibrous tissue in kidney, comprising administering 4-[2-fluoro-4-[[[(2-phenylacetyl)amino]thioxomethyl]amino]-phenoxy]-7-methoxy-N-methyl-6-quinolinecarboxamide or a salt thereof to a patient in need thereof.

2. The method according to claim 1, wherein the abnormal accumulation of a fibrous tissue in kidney is selected from the group consisting of glomerulosclerosis, interstitial renal fibrosis and tubulointerstitial fibrosis.

3. The method according to claim 1, wherein the abnormal accumulation of a fibrous tissue is accompanied by at least one selected from the group consisting of nephritis, renal atrophy and renal failure.

4. The method of claim 1, wherein the 4-[2-fluoro-4[[[(2-phenylacetyl)amino]thioxomethyl]amino]-phenoxy]-7-methoxy-N-methyl-6-quinolinecarboxamide or a salt thereof is orally administered to the patient.

5. The method of claim 1, wherein the salt is a methanesulfonate salt.

6. The method of claim 1, wherein the salt is a monomethanesulfonate salt.

7. The method of claim 1, wherein 0.005 to 5,000 mg of the 4-[2fluoro-4-[[[(2-phenylacetyl)amino]thioxomethyl]amino]-phenoxy]-7-methoxy-N-methyl quinolinecarboxamide or a salt thereof is administered to the patient.

8. The method of claim 1, wherein 0.01 to 1,000 mg of the 4-[2fluoro-4-[[[(2-phenylacetyl)amino]thioxomethyl]amino]-phenoxy]-7-methoxy-N-methyl-6-quinolinecarboxamide or a salt thereof is administered to the patient.

* * * * *